United States Patent [19]

Okazaki et al.

[11] Patent Number: 5,288,616

[45] Date of Patent: Feb. 22, 1994

[54] PROCESS FOR PRODUCING PROTEINS USING SILKWORMS INFECTED WITH RECOMBINANT VIRUS

[75] Inventors: Hironobu Okazaki; Toshimichi Kanaya; Sayuri Nishimura, all of Matsumoto, Japan

[73] Assignee: Katakura Industries Co., Ltd., Tokyo, Japan

[21] Appl. No.: 882,542

[22] Filed: May 13, 1992

[30] Foreign Application Priority Data

Feb. 17, 1992 [JP] Japan ................................. 4-061521

[51] Int. Cl.$^5$ ............................................. C12N 15/00
[52] U.S. Cl. ................................. 435/69.1; 435/320.1
[58] Field of Search ................. 435/69.1, 235.1, 240.2, 435/320.1

[56] References Cited

U.S. PATENT DOCUMENTS

| | | | |
|---|---|---|---|
| 5,017,478 | 5/1991 | Cashion et al. | 435/240.2 |
| 5,041,379 | 8/1991 | Fraser et al. | 435/235.1 |
| 5,110,729 | 5/1992 | Maeda et al. | 435/235.1 |
| 5,118,616 | 6/1992 | Maeda et al. | 435/235.1 |
| 5,155,037 | 10/1992 | Summers | 435/240.2 |

OTHER PUBLICATIONS

Sonobe, H., et al., "Zoological Science," vol. 6, 1989, pp. 515-521.
Singh, S. P., et al., "Boletin de Fisiologia Animal," vol. 9, 1985, pp. 95-102.
Singh, S. P., et al., "Archives Internationales de Physiologie et de Biochimie," vol. 92, 1984, pp. 81-84.
Niimi, T., et al., "Comp. Biochem. Physiol.," vol. 102B(1), 1992, pp. 169-173.
Iwashita, Y., et al., "Bulletin of the College of Agriculture Utsunomiya University," vol. 9(3), Mar. 1976, pp. 11-29. (Full reference of Ueno cited abstract (R) and translation).
Matsubara, F., et al., "Economic Entomology," of Biological Abstr., vol. 80(1), #2720 (abs).
Mori, et al., "Isolation of CDNA Clones Coding for Humoral Lectin of Silkworm, *Bombyx mori* Larvae," Biological Abstracts, 93(7), #77599, 1992, p. 572.
Chernish, S. I., et al., "Adaptation to the Damage in the Silkworm *B. Mori* (Lepodoptera, Bombycidae): III. Adaptogers and Resistance of Caterpillars to Stress-Induced Activation of Latent Viral Infection," Biological Abstracts, 81(5), #41809, 1985.
Matsubara, F., et al., "Resistance to Viral Infection of Silkworm Larvae Reared on Artificial Diet Given Once During the 1st to 3rd Instars," Biological Abstracts, 87(12), pp. 298-299, #124531, 1989.

*Primary Examiner*—Douglas W. Robinson
*Assistant Examiner*—Kristin Larson
*Attorney, Agent, or Firm*—Oblon, Spivak, McClelland, Maier & Neustadt

[57] ABSTRACT

An economic protein can be produced by using silkworms. The silkworms are chilled, warmed, and then orally infected with a virus in which a gene coding the target protein has been inserted. The silkworms so infected are then raised, followed by the collection of the target protein from the silkworms.

3 Claims, No Drawings

PROCESS FOR PRODUCING PROTEINS USING SILKWORMS INFECTED WITH RECOMBINANT VIRUS

BACKGROUND OF THE INVENTION

1) Field of the Invention

This invention relates to a process for producing an economic protein by using silkworms, and more specifically to a process for producing an economic protein by efficiently infecting silkworms p.o. with a virus in which a gene coding the target protein has been inserted (hereafter called the "recombinant virus").

2) Description of the Related Art

In recent years, active research has been conducted with respect to the technology for producing an economic protein with silkworms by making use of recombinant DNA technology. For example, processes using silkworm nuclear polyhedrosis virus as a vector have been reported (Japanese Patent Application Laid-Open Nos. 9288/1986 and 208276/1987, etc.).

According to these processes, a recombinant virus is created by replacing the polyhedral gene of silkworm nuclear polyhedrosis virus with another gene which codes an economic substance. Silkworms of fifth instar are inoculated and infected with the recombinant virus. Four to eight days later, the economic substance which has been produced by the recombinant virus in silkworm cells and secreted in the body fluid in the course of growth of the recombinant virus is collected, isolated and then purified.

Such recombinant DNA technology, which uses silkworms, is considered preferable from the standpoints of the activity, antigenicity and the like of the economic substances to be produced, because the silkworm as a host is closer genetically to man than *Escherichia coli* and yeast which have been used conventionally.

Conventional silkworm-dependent recombinant DNA methods are, however, accompanied by serious problems.

As a method for infecting and inoculating silkworms with a recombinant virus, two methods have been studied, one being the cutaneous infection method in which silkworms are injected one by one with a suspension of the virus to infect them with the virus, and the other the oral infection method in which a suspension of the virus is added to the silkworms' feed to infect them via the digestive tract.

Of these methods, the oral infection method is extremely efficient for the mass production of an economic substance as infection can be completed, for example, by coating artificial feed with a virus suspension and administering it in one episode. This is however not the case, for example, when silkworm nuclear polyhedrosis virus is employed. The recombinant virus produces a target protein in place of a polyhedral protein which is supposed to envelope the virus itself and hence to protect it from dry air and ultraviolet rays in the external atmosphere and, when administered to the silkworm, from the digestive juice of the silkworm. The recombinant virus taken into the digestive tract of the silkworm by the oral infection method is readily inactivated by the digestive juice of the silkworm, so that the silkworm is not infected by it at all.

For the reasons mentioned above, it is the common practice that infection by a recombinant virus is conducted by cutaneous infection. According to cutaneous infection, silkworms must be injected one by one immediately after their ecdysis and, moreover, the injection requires skill and time as it must be performed without damages to various organs in the body of silkworm. Cutaneous infection, therefore, can by no means be adopted for the industrial production of an economic substance.

SUMMARY OF THE INVENTION

To practice the silkworm-dependent recombinant DNA technology in industrial production, there is accordingly an outstanding desire for the establishment of an easy method for efficiently infecting silkworms with a recombinant virus.

The present inventors have proceeded with an extensive investigation to develop a means for sufficiently infecting silkworms with a recombinant virus by oral administration. As a result, it has been found that the activity of the digestive tract of silkworm is lowered after chilling treatment and the oral administration of a recombinant virus in this stage makes it possible to achieve similar infection to that available by injection, leading to the completion of the present invention.

This invention therefore relates to a process for producing an economic protein by using silkworms. More specifically, the present invention provides a process for producing an economic protein by using silkworms, which comprises: subjecting the silkworms to chilling treatment; orally infecting the silkworms with a virus in which a gene coding the target protein has been inserted; raising the silkworms; and collecting the target protein from the silkworms. The chilling treatment of the silkworms may be conducted preferably at 0°-10° C. for 3-36 hours.

According to the process of this invention, a number of silkworms can be infected with a recombinant virus by a simple method, i.e., oral administration so that an economic protein can be obtained efficiently. The process of this invention is, therefore, extremely advantageous from the industrial standpoint than the conventional injection-relying infection method.

DETAILED DESCRIPTION OF THE INVENTION AND PREFERRED EMBODIMENTS

To practice the present invention, silkworms must be subjected to chilling treatment first of all.

No particular limitation is imposed on silkworm usable in the present invention. It is possible to use any species which is available widely. For example, hybrids such as "Shuko x Ryuhaku", "Kinshu x Showa" and "Fuyo x Tokai" can be used suitably. Raising with artificial feed is preferable because silkworms can be raised under sterile conditions. It is therefore desirable to use silkworms which have been found free from pebrine or the like by the pebrine inspection of mother moths.

To raise silkworms under sterile conditions, it is preferable to use silkworm eggs sterilized with disinfectant alcohol, a formaldehyde solution or a sodium hypochlorite solution. Under sterile conditions, these eggs are incubated at suitable temperature and humidit while being exposed to light and are then hatched. Silkworm larvae are then raised in a sterile environment while using sterile feed. The degrees of growth of these silkworm larvae are rendered equal during the molting of fourth instar. The newly exuviated larvae of fifth instar are then employed. Depending on the desired protein, sterile raising is not absolutely needed so that silkworms fed with usual mulberry leaves may be used.

The chilling treatment of silkworms can be conducted suitably at 0°–10° C., with 2°–8° C. being preferred. The suitable treatment time may range from 6 hours to 36 hours. There is a correlation between the temperature of the chilling treatment and its time. At a low temperature of 2.5° C., for example, the infection rate reaches the highest when treated for 12 hours. Treatment for 24 hours is, however, most appropriate for 5° C.

A recombinant virus is then orally administered to the silkworms which have already been subjected to the chilling treatment as described above.

As the preferred method of oral administration of the recombinant virus, the virus is administered together with the silkworm's feed. Specifically, the oral administration method comprises the following steps:

(i) warming the silkworms, which have been subjected to a chilling treatment, to room temperature (25° C.), and (ii) after the silkworms have awaken from the temporary diapause caused by the chilling treatment, feeding the silkworms with articial feed coated or impregnated with the recombinant virus, so that the silkworms become infected.

The recombinant virus can be added to the artificial feed in the following manner. The artificial feed (for example, shape: 5 mm thick×10 mm wide×20 mm long) in an amount of 1 g per silkworm larva is surface-coated or impregnated with a suitable amount of a suspension of the recombinant virus. The silkworms are then allowed to eat the artificial feed.

Commercially-available artificial feed can be used. Although the artificial feed may suitably be in the form of sweet bean jelly having a water content of 65–70%, use of such pellet-like, porous, dry feed as permitting uniform absorption of a virus suspension is preferred because it enables easy and accurate administration of the virus in a desired dose. Only one administration is needed, which can be given to silkworm larvae of early fifth instar. It is then only necessary to raise the silkworm larvae for 4–6 days under conventional raising conditions.

The dose of the virus to be administered to the silkworms varies depending of the recombinant virus and the economic protein to be produced. As a standard, for example, when silkworm nuclear polyhedrosis virus is used, artificial feed in such an amount that each silkworm larva of early fifth instar can eat up completely in 24 hours (about 1 g or so per silkworm larva) may be coated or impregnated with 100 µl of a suspension of the virus prepared at a concentration of $1 \times 10^4$ to $1 \times 10^7$ PFU/µl or so.

Illustrative recombinant virus usable in the present invention includes that obtained by inserting a desired economic protein in the structural gene of the polyhedron protein of the DNA of silkworm nuclear polyhedrosis virus (BmNPV DNA). The silkworm nuclear polyhedrosis virus usable in this invention is that obtained by isolating a strain, which grows actively and forms polyhedron well, from wild-type virus strains and cloning the same through several operations of plaque formation. Typical known examples include T3 strain (ATCC) and P4E strain (National Institute of Sericultural and Entomological Science, Ministry of Agriculture, Forestry and Fisheries, the Government of Japan).

Preparation of the recombinant virus can be conducted in a manner known Per se in the art. For example, an expression promoter (plasmid) for the polyhedron protein of silkworm nuclear polyhedrosis virus is prepared. A gene coding a desired economic protein is inserted under the control of the plasmid to prepare an expression vector. The expression vector and silkworm nuclear polyhedrosis virus, which has been cloned, are next co-transfected to established silkworm cells, so that the resulting transformed recombinant virus is cultured and allowed to grow in the same established silkworm cells. The cells are then disrupted to obtain the recombinant virus.

In the present invention, examples of an economic protein whose gene is inserted in a recombinant virus can include enzymes such as urokinase, angiotensin transferase, $\alpha$-amidase and cytochrome P-450; hormones such as insulin, somatomedin, human growth hormone and various animal growth hormones; cytokines such as interferons ($\alpha$, $\beta$ and $\gamma$), interleukin (1–7), CSF and EPO; various virus proteins such as gp160 (gp120, gp40) of AIDS virus, HA protein of influenza, HBs of hepatitis B virus, HCs of hepatitis C virus and gp50 of rabies virus; receptor proteins of various cells, such as CD4 of T cell, C-fms and erbB; nuclear proteins such as myf and fos; peptides such as various physiologically active substances; proteins and glycoproteins.

Known examples of established silkworm cells include Bm cells (ATCC CRL-9810), Bm-N cells (ATCC CRL-8851) and Bm 36 cells. When Bm-N cells are used, it is suitable to obtain the recombinant virus by freezing cells subsequent to co-transfection and then thawing and disrupting the thus-frozen cells. When Bm 36 cells are used, the recombinant virus can be obtained from the supernatant of a culture broth.

After the recombinant virus has been administered orally as described above, the silkworms are raised until the recombinant virus grows inside the bodies of the silkworms.

Suitably, the raising temperature may range from 22° C. to 28° C. When raised at a desired constant temperature, the target protein can always be obtained stably within the same number of days of culture. When raised, for example, at the constant temperature of 25° C. using silkworm polyhedrosis virus as a recombinant virus, the silkworm larvae so infected show pathological symptoms typical to nuclear polyhedrosis on the fifth day after administration.

A raising vessel capable of maintaining a sterile environment is preferred. It is desirable to use, for example, a vessel which is closed by an air-permeable lid equipped with a bacterial filter.

Regarding the number of silkworm larvae to be raised in a vessel, it is suitable to raise, for example, 20–40 fifth instar larvae in a vessel of 200 mm wide×250 mm long×50–100 mm high.

Everyday feeding is not required. Feed for 2–3 days can be given in an episode. The total amount of feed from the administration of the recombinant virus until the recovery of the target protein may range from about 8 g to about 12 g per silkworm larva although it varies depending on the water content of the feed (equivalent to about 2.5–4.0 dry grams per silkworm larva).

The recovery and isolation of the target protein produced inside the body of each silkworm larva can be effected by collecting the body fluid of the silkworm larva on the 4th to 6th day after the infection, on which day the target protein is accumulated most abundantly in the body of the silkworm larva, and collecting and purifying the economic protein by various isolation means such as centrifugation and column chromatography. As an alternative, the silkworm larvae are ground and then extracted in an aqueous SDS solution, an aqueous urea solution, an aqueous alkaline solution or the like, followed by the isolation and collection of the economic protein in a manner commonly employed in the art. As a still further alternative, ground silkworm larvae are suspended in a phosphate buffer or the like. Subsequent to ultrasonic processing, a substance capable of specifically binding the target economic protein, such as red blood cells, is added to obtain the economic protein.

The present invention will next be described in further detail by a referential example and examples. It is however to be noted that the present invention is not limited by the following examples.

REFERENTIAL EXAMPLE

Preparation of Recombinant Virus

As a representative strain of silkworm nuclear polyhedrosis virus (Bm NPV), there is T3 strain. The virus DNA (Bm NPV DNA) of this strain has been deposited under ATCC 40188 with the American Type Culture Collection (ATCC), U.S.A. Further, *Escherichia coli* (*E. coli* K12 JM83 DGB-0036)—which contains plasmid pBmE 36 with an EcoRI-EcoRI fragment (about 10.5 kb) of the above virus DNA introduced at the EcoRI cleavage site of pBR322 - has been deposited under FERM BP-813 with Fermentation Research Institute, Agency of Industrial Science and Technology, Ministry of Industrial Trade and Industry, the Government of Japan.

The recombinant plasmid employed for the present invention is prepared based on the disclosure of the publication, "Nature", 315, 592 (1985).

Namely, pBmE 36 is treated with HindIII to obtain a fragment of about 3.9 kbp long, said fragment containing the structural gene of the polyhedron protein. The fragment is inserted in commercial plasmid pUC 9 (product of Pharmacia PL Biochemical Inc.). The plasmid so transformed is then manipulated, namely, is digested with EcoRI, treated with Bal31 and then cleaved with HindIII, whereby a fragment containing the entire portion or a portion of the gene of the polyhedron protein is prepared. This fragment is then inserted in pUC 9. On the side, a plasmid containing flanking sequences is prepared. They are combined together so that a further plasmid (for example, a plasmid of the p98B series) can be formed. The plasmid is then digested with BamHI and PstI, followed by the isolation of a 5.3 kbp DNA fragment containing a pUC-derived skeleton. The DNA fragment is then spliced with a 3.7 kbp DNA fragment which has been obtained by digesting plasmid pBM 030 [see "Agric. Biol. Chem.", 51, 1573–1580 (1987)] with BamHI and PstI, so that a plasmid (for example, pBM 050) can be prepared.

The HA gene of an influenza virus is cut out from an HA-gene-containing plasmid [for example, PEH-HAI (deposited as "*E. coli* EH-HAI" under the deposit number of FERM BP-2585 with Fermentation Research Institute, Agency of Industrial Science and Technology, Ministry of Industrial Trade and Industry, the Government of Japan)] and is inserted in the plasmid obtained above. A plasmid with the fragment inserted in the correct direction is chosen as a recombination plasmid (expression vector).

To produce a recombinant virus by using the recombination plasmid obtained above, the established silkworm cell strain Bm-N is subjected to co-transfection with the recombination plasmid and the nuclear polyhedrosis virus DNA of silkworm. The resulting recombinant virus is then isolated by the plaque assay ["J. Seric. Soc. Jpn.", 53, 547 (1984)], the dilution end point technique ["J. Invertebr. Pathol.", 29, 304 (1977)] or the like. This operation is repeated to purify the recombinant virus.

After the recombinant virus purified as described above is infected to Bm-N cells and is allowed to grow therein, the Bm-N cells are stored at $-80°$ C. The infection rate ($TCID_{50}$) of the cells with the recombinant virus is measured, and the culture broth so obtained is provided as a base virus suspension.

The potency of the virus suspension obtained as a result of the growth of the virus in the Bm-N cells was 3.4 in terms of infection rate ($TCID_{50}$), and the content of the virus was about $2 \times 10^7$ PFU/$\mu$l.

In the case of oral administration in this invention, artificial feed in the amount of 1 g per silkworm larva was coated with 100 $\mu$l of a 10-fold dilute solution of the virus suspension and was given to silkworms.

EXAMPLE 1

Infection Test with A Recombinant Virus

An infection test with a recombinant virus was conducted using, as the recombinant virus, a virus containing the HA protein gene, which had been prepared by the method described above, and capable of expressing the HA protein gene and, as a test silkworm, "Shuko x Ryuhaku" raised with artificial feed. Namely, forty test silkworm larvae which had been made equal in stage at the early fifth instar were provided per group and treated under the chilling conditions shown in Table 1. Namely, the chilling temperature was set at 2.5° C., 5° C., 10° C. and 15° C., while the chilling time was set at 6 hours, 12 hours, 24 hours and 36 hours. Treatment was conducted under various combinations of those chilling temperatures and chilling times. After the chilling treatment, the temperature was raised back to 25° C., and artificial feed was coated with 100 $\mu$l of the recombinant virus suspension having a virus concentration of about $2 \times 10^6$ PFU/$\mu$l per gram of the artificial feed and then given to the silkworms to infect the silkworms. The silkworms were then raised under the temperature condition of 25° C. while feeding normal artificial feed, and the infection rate was investigated.

Each silkworm larva on the 5th day or so after the infection with the virus showed pathological symptoms induced by Bm NPV, which is typical to silkworm. In other words, they showed the pathological symptoms that their bodies were constricted between segments and became transparent as a whole in outer experience and they feebly writhed. As they would soon die if left over as they were, the body fluid of the silkworm was collected before the silkworm died and the HA value was measured by the procedures to be describe next.

Measurement method of HA value

The silkworms were added with PBS (phosphate buffer) in an amount of 15 ml per silkworm larva, disrupted in a homogenizer, and then disrupted further for a limited time (about 1 minute) in an ultrasonic disrupting machine. The disrupted silkworm suspension was then centrifuged at 3,000 rpm for 10 minutes. The resulting supernatant was provided as a sample stock.

Using PBS, two-fold serial dilution of the sample stock was conducted on a 96-well plate in which each well had a U-shaped bottom (50 μl were placed in each well). To each well, 50 μl of a 0.5% fowl red cell suspension was added, and the plate was shaken sufficiently. After reaction at room temperature for 1 hour, each reaction mixture was observed for possible coagulation of red blood cells. The maximum dilution in terms of times at which coagulation was observed was recorded as the HA value of the sample stock. Forty silkworms were tested per test group. Measurement was conducted four times, and the HA value indicates the average of the data so measured.

TABLE 1

| Test group number | Conditions for chilling treatment | | Infection rate on the fifth day (%) | Weight on the fifth day (g) | HA value |
|---|---|---|---|---|---|
| | Temp. (°C.) | Time (hr) | | | |
| 1 | (No chilling treatment) | | 0 | 5.2 | 0 |
| 2 | 2.5 | 6 | 55 | 4.8 | 4,096 |
| 3 | 2.5 | 12 | 100 | 5.0 | 8,192 |
| 4 | 2.5 | 24 | 100 | 4.8 | 8,192 |
| 5 | 2.5 | 36 | 90 | 3.8 | 4,096 |
| 6 | 5 | 6 | 35 | 5.0 | 2,048 |
| 7 | 5 | 12 | 95 | 4.8 | 7,168 |
| 8 | 5 | 24 | 100 | 4.8 | 8,192 |
| 9 | 5 | 36 | 100 | 4.6 | 8,192 |
| 10 | 10 | 6 | 20 | 5.1 | 640 |
| 11 | 10 | 12 | 50 | 5.0 | 3,584 |
| 12 | 10 | 24 | 65 | 4.8 | 5,120 |
| 13 | 10 | 36 | 80 | 4.7 | 6,144 |
| 14 | 15 | 6 | 0 | 4.9 | 0 |
| 15 | 15 | 12 | 0 | 5.0 | 0 |
| 16 | 15 | 24 | 2.5 | 4.6 | 64 |
| 17 | 15 | 36 | 5.0 | 4.2 | 128 |
| 18* | (Control) | | 100 | 4.8 | 8,192 |

*Control: A recombinant virus suspension having a virus concentration of $2 \times 10^4$ PFU/μl was coelomically administered by injection at a dose of 50 μl per silkworm larva.

From the above results, it has been found that chilling treatment permits infection with a recombinant virus even by oral administration and similar results to infection by injection can be obtained.

In addition, the following findings have also been obtained.

(1) When subjected to treatment at the low temperature of 2.5° C. for a long time (36 hours), physiological disorder is observed including a reduction in the amount of eaten feed.
(2) At 10° C., effects of infection begin to appear as the treatment time becomes longer.
(3) At 15° C., no substantial effects of infection are observed.

What is claimed is:

1. A process for producing a protein using silkworms, which comprises:
   chilling the silkworms to a temperature of from 0 to 10° C.;
   allowing the chilled silkworms to warm to about 25° C. to awaken the silkworms from a temporary diapause caused by said chilling step;
   orally administering to said silkworms a feed containing a recombinant Bm nuclear polyhedrosis virus in an amount effective to infect the silkworms into which has been inserted a gene encoding said protein;
   raising said silkworms;
   and isolating said protein from said silkworms.

2. The process of claim 1, wherein the chilling treatment of the silkworms is conducted at 2°-8° C.

3. The process of claim 1, wherein the chilling treatment of the silkworms is conducted for 3-36 hours.

* * * * *